(12) United States Patent
Noguchi et al.

(10) Patent No.: US 8,855,941 B2
(45) Date of Patent: Oct. 7, 2014

(54) METHOD FOR EXAMINING PROGNOSIS OF BREAST CANCER

(75) Inventors: Shinzaburou Noguchi, Osaka (JP); Yasuto Naoi, Minoh (JP); Kazuki Kishi, Ashiya (JP); Kengo Gotoh, Kobe (JP)

(73) Assignees: Osaka University, Osaka (JP); Sysmex Corporation, Hyogo (JP)

( * ) Notice: Subject to any disclaimer, the term of this patent is extended or adjusted under 35 U.S.C. 154(b) by 401 days.

(21) Appl. No.: 13/091,716

(22) Filed: Apr. 21, 2011

(65) Prior Publication Data

US 2011/0263444 A1 Oct. 27, 2011

(30) Foreign Application Priority Data

Apr. 22, 2010 (JP) .................................. 2010-098935

(51) Int. Cl.
| | |
|---|---|
| *G01N 33/48* | (2006.01) |
| *C12Q 1/68* | (2006.01) |
| *G06F 19/20* | (2011.01) |
| *G06F 19/24* | (2011.01) |

(52) U.S. Cl.
CPC ............... *G06F 19/20* (2013.01); *G06F 19/24* (2013.01); *C12Q 2600/118* (2013.01); *C12Q 2600/158* (2013.01); *C12Q 1/6886* (2013.01)
USPC .......................................................... 702/20

(58) Field of Classification Search
USPC .......................................................... 702/20
See application file for complete search history.

(56) References Cited

FOREIGN PATENT DOCUMENTS

| JP | 2007-528218 A | 10/2007 |
|---|---|---|
| JP | 2009-131262 A | 6/2009 |
| WO | 02/103320 A2 | 12/2002 |
| WO | 2005/083429 A2 | 9/2005 |

OTHER PUBLICATIONS

Sotiriou Christos, et al., "Gene Expression Profiling in Breast Cancer: Understanding the Molecular Basis of Histologic Grade to Improve Prognosis", Journal of the National Cancer Institute, Feb. 15, 2006, pp. 262-272, vol. 98, No. 4.
van't Veer et al., "Gene expression profiling predicts clinical outcome of breast cancer", Nature, vol. 415, No. 6871, pp. 530 to 536 (2002).
Noguchi, S., "Individuality diagnosis of breast cancer and elucidation of molecular pathogenesis", Grant-in-Aid for Scientific Research on Priority Areas Cancer, Ministry of Education, Culture, Sports, Science and, Technology, p. 248 (2008).
Akashi, S. And K. Terada, "Chapter 1. Diagnosis based on gene polymorphism, mutation, and gene expression information: Diagnosis using gene expression information in cancer," Jikken Igaku, vol. 25, No. 17, pp. 58 to 62, (2007).
Brennan et al., "Application of DNA microarray technology in determining breast cancer prognosis and therapeutic response", Expert Opinion on Biological Therapy, vol. 5, No. 8, pp. 1069-1083, (2005).
Culhane et al., "Between-group analysis of microarray data", Bioinformatics, vol. 18, No. 10, pp. 1600-1608 (2002).

*Primary Examiner* — Jerry Lin
(74) *Attorney, Agent, or Firm* — Sughrue Mion, PLLC

(57) ABSTRACT

Disclosed is a method for examining prognosis of breast cancer including the steps of: (A) extracting RNA from a specimen collected from a subject, (B) preparing a determination sample using the extracted RNA, (C) determining the expression level of each gene in the specific gene groups using the obtained determination sample, (D) analyzing the expression level of the determined each gene, and (E) examining prognosis of breast cancer, based on the obtained analysis result are performed.

2 Claims, 5 Drawing Sheets

FIG. 2

|  |  | Prediction result by discriminant | |  |  |
|---|---|---|---|---|---|
|  |  | no recurrence | recurrence |  |  |
| Observation result | no recurrence | 57 | 24 | specificity | 70.4% |
|  | recurrence | 4 | 20 | sensitivity | 83.3% |
|  |  |  |  |  |  |
|  |  | NPV | PPV |  |  |
|  |  | 93.4% | 45.5% |  |  |

METHOD FOR EXAMINING PROGNOSIS OF BREAST CANCER

TECHNICAL FIELD

The present invention relates to a method for examining prognosis of breast cancer.

BACKGROUND ART

In about ⅔ cases of primary breast cancer cases, estrogen receptor (ER) is present in breast cancer cells (referred to as "ER-positive"). In ER-positive breast cancer cells, binding of estrogen to ER contributes to cell proliferation.

Therefore, in the treatment for node-negative and ER-positive breast cancer patients, hormonal therapy targeting ER plays an important role.

In hormonal therapy for the node-negative and ER-positive breast cancer patients, metastasis of breast cancer and recurrence are suppressed by, for example, administering an anti-estrogen such as tamoxifen to the patients, thereby blocking the binding of estrogen to ER in the breast cancer cells to suppress proliferation of breast cancer cells. In the case where the above patients are treated with the above hormonal therapy, most of the patients show comparatively good prognosis.

However, about 20% of the above patients may have a recurrence of breast cancer.

Therefore, in order to reduce the recurrence rate, most of the node-negative and ER-positive breast cancer patients are treated with not only hormonal therapy but also adjuvant chemotherapy at present, even though chemotherapy is considered to be unnecessary for the node-negative and ER-positive breast cancer patients in most cases.

Thus, it seems to be important to predict the prognosis of the node-negative and ER-positive breast cancer patients in order to provide adjuvant chemotherapy only to patients who are at high risk for recurrence.

Recently, based on an analysis of comprehensive gene expression profile, prediction of breast cancer prognosis in a breast cancer patient has been attempted (see, for example, Patent Literatures 1 and 2, Non Patent Literature 1 and the like).

The Patent Literature 1 describes a method for classifying a breast cancer patient into a patient having "no distant metastases within five years from the time of initial diagnosis" or a patient having "distant metastases within five years from the time of initial diagnosis", using gene markers identified by using tumor samples of 117 breast cancer patients, based on the difference between the gene marker expression in a cell sample of a breast cancer patient and the gene marker expression in a control. In addition, the Patent Literature 1 describes that as the gene markers, a gene marker capable of distinguishing the presence or absence of ER, a gene marker capable of distinguishing between tumors having a mutation of BRCA1 gene and sporadic tumors, and a gene marker capable of distinguishing between a patient having "no distant metastases within five years from the time of initial diagnosis" and a patient having "distant metastases within five years from the time of initial diagnosis" are used.

In addition, the Patent Literature 2 describes a method for diagnosing prognosis, comprising the steps of obtaining gene expression profile in the biological samples of breast cancer patients, with the use of 76 genes providing an indication of prognosis, the genes being identified by using tumor samples of 286 node-negative breast cancer patients, and comparing the expression level obtained from the gene expression profile with the predetermined cut-off levels.

Furthermore, the Non Patent Literature 1 describes a method for predicting a prognosis, wherein cases of breast cancer conventionally classified as histological grade 2 is further classified into a high-risk group for recurrence and a low-risk group for recurrence by using Genomic Grade Index (GGI) based on 97 genes, the genes being identified by using 189 cases of invasive breast cancer patients and three known gene expression datasets of breast cancer.

SUMMARY OF INVENTION

However, since these methods are affected by the difference between institutions examined, the difference between races and the like, these methods cannot always properly predict prognosis at present.

The present invention has been made in view of the above conventional arts, and an object of the present invention is to provide a method for examining prognosis of breast cancer, which can properly predict prognosis.

More specifically, the present invention relates to:
{1} a method for examining prognosis of breast cancer comprising the steps of:
(A) extracting RNA from a specimen collected from a subject,
(B) preparing a determination sample using the RNA extracted in the step (A),
(C) determining the expression level of each gene in the gene groups described in Table 1-1 and Table 1-2 using the determination sample obtained in the step (B),
(D) analyzing the expression level of each gene determined in the step (C), and
(E) examining prognosis of breast cancer, based on the analysis result obtained in the step (D);
{2} the method for examining prognosis of breast cancer according to the above item {1}, wherein the expression level is analyzed by using a classification method, in the step (D);
{3} the method for examining prognosis of breast cancer according to the above item {2}, wherein the classification method is Between-group analysis;
{4} the method for examining prognosis of breast cancer according to the above item {1}, comprising the steps of:
calculating solution D of a discriminant using the expression level and the discriminant represented by the following formula (1):

$$D = \frac{\sum_i w_i \times X_i}{\sum_i X_i} - 0.0061 \qquad (1)$$

in the step (D), and
predicting poor prognosis when the solution D of the discriminant is a positive value, and good prognosis when the solution D is 0 or a negative value, in the step (E),
wherein i in the formula (1) shows the gene number provided to the nucleic acid described in Table 1-1 and Table 1-2, $w_i$ in the formula (1) shows a weight coefficient corresponding to the nucleic acid with gene number i described in Table 1-1 and Table 1-2, $X_i$ in the formula (1) shows a normalized expression level which is obtained by normalization using the following formula (2):

$$X_i = y_i + \text{abs}[\text{round}\{\min(y_{ij}) - 1\}] \qquad (2)$$

and $$\sum_i$$

shows the summation of each nucleic acid, and wherein j in the formula (2) shows the specimen number provided to each specimen, $y_{ij}$ in the formula (2) shows the standardized expression level in a specimen with specimen number j of a gene corresponding to the nucleic acid with gene number i, min in the formula (2) shows the minimum value of the value in parentheses, round in the formula (2) shows the value obtained by rounding the value in parentheses to the nearest whole number, abs in the formula (2) shows the absolute value of the value in parentheses, $y_i$ in the formula (2) shows a standardized expression level of a gene corresponding to the nucleic acid with gene number i, the standardized expression level being obtained by standardization using the following formula (3):

$$y_i = x_i - u_i \quad (3)$$

wherein $x_i$ in the formula (3) shows the expression level of a gene corresponding to the nucleic acid with gene number i, and $u_i$ in the formula (3) shows the average value of specimens of the expression level of a gene corresponding to the nucleic acid with gene number i;

{5} the method for examining prognosis of breast cancer according to the above item {1}, wherein the expression level is analyzed by a hierarchical cluster analysis, in the step (D);

{6} the method for examining prognosis of breast cancer according to the above item {1}, wherein the expression level is analyzed by a scoring method, in the step (D); and {7} the method for examining prognosis of breast cancer according to any of the above item {1}, wherein the expression level is determined by using a microarray having at least the nucleic acid described in Table 1-1 and Table 1-2.

According to the method for examining prognosis of breast cancer of the present invention, an excellent effect such that prognosis can be properly predicted is exhibited.

BRIEF DESCRIPTION OF DRAWINGS

FIG. 2 is a chart showing the result of comparing the prediction result by a discriminant with the observation result for 105 cases of breast cancer patients in Example 2.

DESCRIPTION OF EMBODIMENTS

Figure 1:
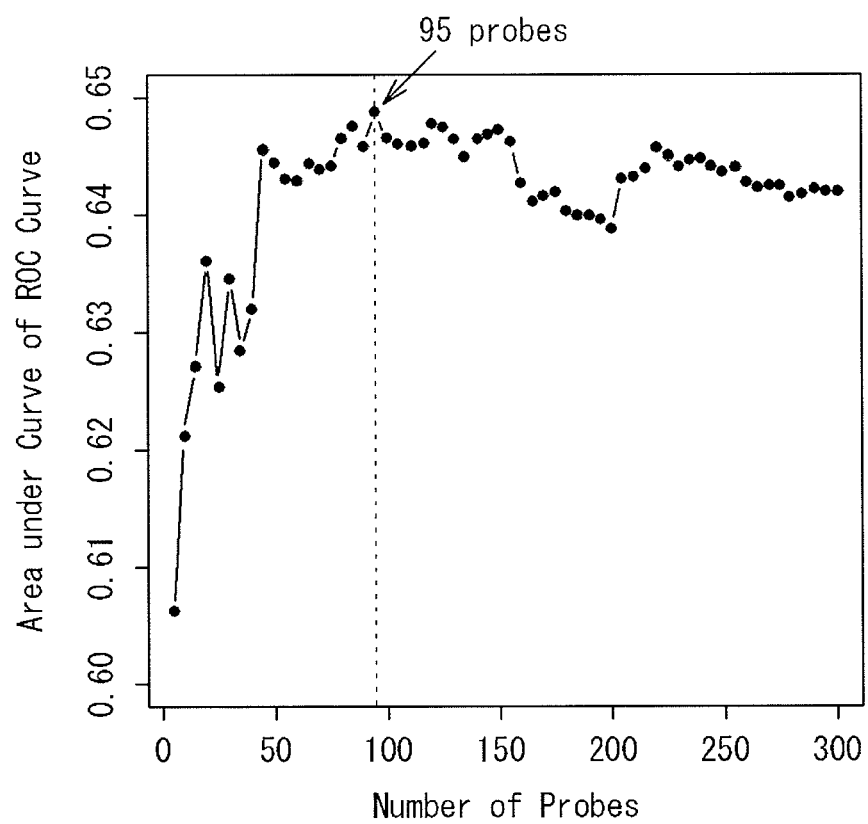
FIG. 1 is a graph showing the result of examining a relationship between the number of probes and the area under the curve of ROC curve in Example 1.

The method for examining prognosis of breast cancer of the present invention includes the steps of:

(A) extracting RNA from a specimen collected from a subject, (B) preparing a determination sample using the RNA extracted in the step (A), (C) determining the expression level of each gene in the gene groups described in Table 1-1 and Table 1-2 using the determination sample obtained in the step (B), (D) analyzing the expression level determined in the step (C), and (E) examining prognosis of breast cancer, based on the analysis result obtained in the step (D).

TABLE 1-1

| Gene Number | Probe Set. ID | Gene Symbol | UniGene.ID | GenBank Accession Number | Weight Coefficient |
|---|---|---|---|---|---|
| 1 | 219306_at | KIF15 | Hs.646856 | NM_020242 | 0.5960 |
| 2 | 218585_s_at | DTL | Hs.656473 | NM_016448 | 1.4097 |
| 3 | 221677_s_at | DONSON | Hs.436341 | AF232674 | 0.4683 |
| 4 | 201088_at | KPNA2 | Hs.594238 | NM_002266 | 1.0480 |
| 5 | 209034_at | PNRC1 | Hs.75969 | AF279899 | −1.4059 |
| 6 | 202610_s_at | MED14 | Hs.407604 | AF135802 | −0.0393 |
| 7 | 218906_x_at | KLC2 | Hs.280792 | NM_022822 | 0.0880 |
| 8 | 212723_at | JMJD6 | Hs.514505 | AK021780 | 0.3141 |
| 9 | 222231_s_at | LRRC59 | Hs.370927 | AK025328 | 0.6264 |
| 10 | 208838_at | CAND1 | Hs.546407 | AB020636 | 0.2207 |
| 11 | 218039_at | NUSAP1 | Hs.615092 | NM_016359 | 1.5846 |
| 12 | 209472_at | CCBL2 | Hs.481898 | BC000819 | −1.7235 |
| 13 | 212898_at | KIAA0406 | Hs.655481 | AB007866 | 0.1172 |
| 14 | 202620_s_at | PLOD2 | Hs.477866 | NM_000935 | 1.3605 |
| 15 | 201059_at | CTTN | Hs.596164 | NM_005231 | 0.3591 |
| 16 | 201841_s_at | HSPB1 | Hs.520973 | NM_001540 | 1.2420 |
| 17 | 203755_at | BUB1B | Hs.631699 | NM_001211 | 0.9909 |
| 18 | 211750_x_at | TUBA1C | Hs.719091 | BC005946 | 0.0145 |
| 19 | 38158_at | ESPL1 | Hs.153479 | D79987 | 0.5325 |
| 20 | 204709_s_at | KIF23 | Hs.270845 | NM_004856 | 0.0798 |
| 21 | 201589_at | SMC1A | Hs.211602 | D80000 | 0.3106 |
| 22 | 218460_at | HEATR2 | Hs.535896 | NM_017802 | 0.0198 |
| 23 | 207430_s_at | MSMB | Hs.255462 | NM_002443 | 1.9177 |
| 24 | 212139_at | GCN1L1 | Hs.298716 | D86973 | −0.0501 |
| 25 | 211596_s_at | LRIG1 | Hs.518055 | AB050468 | −2.0999 |
| 26 | 212160_at | XPOT | Hs.85951 | AI984005 | 0.3461 |
| 27 | 219238_at | PIGV | Hs.259605 | NM_017837 | −1.2689 |
| 28 | 203432_at | TMPO | Hs.11355 | AW272611 | 0.4665 |
| 29 | 201377_at | UBAP2L | Hs.490551 | NM_014847 | 0.1269 |

TABLE 1-1-continued

| Gene Number | Probe Set. ID | Gene Symbol | UniGene.ID | GenBank Accession Number | Weight Coefficient |
|---|---|---|---|---|---|
| 30 | 218875_s_at | FBXO5 | Hs.520506 | NM_012177 | 0.1012 |
| 31 | 221922_at | GPSM2 | Hs.584901 | AW195581 | 0.4423 |
| 32 | 218727_at | SLC38A7 | Hs.10499 | NM_018231 | −0.0411 |
| 33 | 207469_s_at | PIR | Hs.495728 | NM_003662 | 0.8827 |
| 34 | 218483_s_at | C11orf60 | Hs.533738 | NM_020153 | −1.3198 |
| 35 | 204641_at | NEK2 | Hs.153704 | NM_002497 | 1.5825 |
| 36 | 219502_at | NEIL3 | Hs.405467 | NM_018248 | −0.1883 |
| 37 | 209054_s_at | WHSC1 | Hs.113876 | AF083389 | 0.0465 |
| 38 | 220318_at | EPN3 | Hs.670090 | NM_017957 | 0.3073 |
| 39 | 210297_s_at | MSMB | Hs.255462 | U22178 | 1.6681 |
| 40 | 209186_at | ATP2A2 | Hs.506759 | M23114 | 0.2014 |
| 41 | 219787_s_at | ECT2 | Hs.518299 | NM_018098 | 0.8181 |
| 42 | 45633_at | GINS3 | Hs.47125 | AI421812 | −0.2363 |
| 43 | 200848_at | AHCYL1 | Hs.705418 | AA479488 | −1.5895 |
| 44 | 200822_x_at | TPI1 | Hs.524219 | NM_000365 | 0.0814 |
| 45 | 211072_x_at | TUBA1B | Hs.719075 | BC006481 | 0.0380 |
| 46 | 200811_at | CIRBP | Hs.634522 | NM_001280 | −1.4620 |
| 47 | 202864_s_at | SP100 | Hs.369506 | NM_003113 | −1.3947 |
| 48 | 202154_x_at | TUBB3 | Hs.511743 | NM_006086 | 0.1241 |
| 49 | 213152_s_at | SFRS2B | Hs.476680 | AI343248 | −1.2495 |
| 50 | 209368_at | EPHX2 | Hs.212088 | AF233336 | −1.8835 |

TABLE 1-2

| Gene Number | Probe Set. ID | Gene Symbol | UniGene.ID | GenBank Accession Number | Weight Coefficient |
|---|---|---|---|---|---|
| 51 | 211058_x_at | TUBA1B | Hs.719075 | BC006379 | 0.0646 |
| 52 | 209251_x_at | TUBA1C | Hs.719091 | BC004949 | 0.0453 |
| 53 | 213646_x_at | TUBA1B | Hs.719075 | BE300252 | 0.0396 |
| 54 | 204540_at | EEF1A2 | Hs.433839 | NM_001958 | 1.8487 |
| 55 | 202026_at | SDHD | Hs.719164 | NM_003002 | −1.3587 |
| 56 | 201090_x_at | TUBA1B | Hs.719075 | NM_006082 | 0.0733 |
| 57 | 213119_at | SLC36A1 | Hs.269004 | AW058600 | 0.0680 |
| 58 | 217840_at | DDX41 | Hs.484288 | NM_016222 | 0.0313 |
| 59 | 206559_x_at | EEF1A1 | — | NM_001403 | −0.9727 |
| 60 | 202066_at | PPF1A1 | Hs.530749 | AA195259 | 0.7385 |
| 61 | 203108_at | GPRC5A | Hs.631733 | NM_003979 | 1.0799 |
| 62 | 218697_at | NCKIPSD | Hs.655006 | NM_016453 | −0.0693 |
| 63 | 222039_at | KIF18B | Hs.135094 | AA292789 | 0.6820 |
| 64 | 202069_s_at | IDH3A | Hs.591110 | AI826060 | 0.2302 |
| 65 | 203362_s_at | MAD2L1 | Hs.591697 | NM_002358 | 0.8095 |
| 66 | 202666_s_at | ACTL6A | Hs.435326 | NM_004301 | 0.2162 |
| 67 | 204892_x_at | EEF1A1 | Hs.520703 | NM_001402 | −0.9566 |
| 68 | 205682_x_at | APOM | Hs.534468 | NM_019101 | −1.0558 |
| 69 | 209714_s_at | CDKN3 | Hs.84113 | AF213033 | 0.9594 |
| 70 | 218381_s_at | U2AF2 | Hs.528007 | NM_007279 | −0.0076 |
| 71 | 201947_s_at | CCT2 | Hs.189772 | NM_006431 | 0.2632 |
| 72 | 212722_s_at | JMJD6 | Hs.514505 | AK021780 | 0.0968 |
| 73 | 204825_at | MELK | Hs.184339 | NM_014791 | 1.1379 |
| 74 | 203184_at | FBN2 | Hs.519294 | NM_001999 | 0.7174 |
| 75 | 201266_at | TXNRD1 | Hs.708065 | NM_003330 | 0.2610 |
| 76 | 202969_at | DYRK2 | Hs.173135 | AI216690 | 0.2560 |
| 77 | 204817_at | ESPL1 | Hs.153479 | NM_012291 | 0.4866 |
| 78 | 209523_at | TAF2 | Hs.122752 | AK001618 | 0.3803 |
| 79 | 218491_s_at | THYN1 | Hs.13645 | NM_014174 | −1.3652 |
| 80 | 217363_x_at | — | — | AL031313 | −0.9838 |
| 81 | 218009_s_at | PRC1 | Hs.567385 | NM_003981 | 1.6691 |
| 82 | 204026_s_at | ZWINT | Hs.591363 | NM_007057 | 0.9942 |
| 83 | 218355_at | KIF4A | Hs.648326 | NM_012310 | 1.1017 |
| 84 | 202153_s_at | NUP62 | Hs.574492 | NM_016553 | −0.0983 |
| 85 | 213011_s_at | TPI1 | Hs.524219 | BF116254 | 0.1005 |
| 86 | 217966_s_at | FAM129A | Hs.518662 | NM_022083 | −2.4459 |
| 87 | 214782_at | CTTN | Hs.596164 | AU155105 | 0.2306 |
| 88 | 217967_s_at | FAM129A | Hs.518662 | AF288391 | −2.7067 |
| 89 | 204649_at | TROAP | Hs.524399 | NM_005480 | 0.1495 |
| 90 | 35671_at | GTF3C1 | Hs.371718 | U02619 | 0.0169 |
| 91 | 213502_x_at | LOC91316 | Hs.148656 | AA398569 | −2.1336 |
| 92 | 221285_at | ST8SIA2 | Hs.302341 | NM_006011 | −0.9209 |
| 93 | 221519_at | FBXW4 | Hs.500822 | AF281859 | −1.1897 |
| 94 | 202551_s_at | CRIM1 | Hs.699247 | BG546884 | −2.0141 |
| 95 | 217138_x_at | IGL@ | Hs.449585 | AJ249377 | −1.0505 |

In the present specification, "Probe Set. ID" shows the ID number provided to each probe set putting together 11 to 20 probes immobilized on a substrate in a microarray manufactured by Affymetrix, Inc [trade name: GeneChip (registered trademark) System]. The nucleotide sequence of the nucleic acid (probe set) shown by the above Probe Set. ID is easily available in database disclosed in Affymetrix's web page (database updated on Jun. 30, 2009). "UniGene. ID" shows the ID number of UniGene that is a database published by NCBI. GenBank accession number shows the accession number of the published database GenBank used for designing the sequence of each probe immobilized on a substrate in the above microarray manufactured by Affymetrix, Inc. [trade name: GeneChip (registered trademark) System].

In the present specification, the phrase "the expression level of each gene in the gene groups described in Table 1-1 and Table 1-2" refers to the expression level of a gene having the nucleic acid shown by the GenBank accession number described in Table 1-1 and Table 1-2 corresponding to the Probe Set. ID described in Table 1-1 and Table 1-2. GenBank is a database provided by National Center for Biotechnology Information, and is available for general use. Moreover, the sequence to which the GenBank accession number described in Table 1-1 and Table 1-2 is provided is available from the above database. In addition, the above GenBank accession number shows the number in the latest release as of Jun. 30, 2009. In the present specification, a "gene" may be a unit or part of the nucleotide sequence from which RNA is derived as a gene transcript, and is a concept also including EST (expressed sequence tag).

In the examination method of the present invention, first, RNA is extracted from a specimen collected from a subject [step (A)].

The "subject" refers to a breast cancer patient and a patient suspected of having breast cancer. Here, the breast cancer patient is not particularly limited. The breast cancer patient includes, for example, a node-negative and ER-positive breast cancer patient, and the like. The node-negative and ER-positive breast cancer patient may be a node-negative and ER-positive breast cancer patient treated with hormonal therapy in which an antiestrogen is administered to the patient.

In the examination method of the present invention, for example, in the case where the subject is a node-negative and ER-positive breast cancer patient treated with hormonal therapy that administers an antiestrogen, the prediction such that the patient has good prognosis can be made with a high accuracy. In the present specification, "good prognosis" refers that no recurrence is found for 10 years after surgery.

The specimen includes, for example, a tumor tissue excised during surgery, a specimen collected from a subject by biopsy, and the like.

RNA extraction from a specimen can be performed by a known method. In addition, a commercial kit for extracting RNA can be also used for RNA extraction from a specimen. Here, the commercial kit includes, for example, trade name: Qiagen RNeasy kit (registered trademark), manufactured by Qiagen, and the like.

Next, a determination sample is prepared by using the RNA extracted in the step (A) [step (B)].

In the step (B), a determination sample suitable for determining the gene expression level, in other words, the production amount of transcripts corresponding to the gene (cRNA, cDNA, mRNA, and the like) is prepared. Specifically, the determination sample can be prepared by, for example, amplification of the corresponding cRNA or cDNA using the RNA extracted in the above step (A), purification of mRNA from the RNA extracted in the above step (A), or the like. In addition, in the present invention, when it is possible to determine the gene expression level, the RNA extracted in the above step (A) may be directly used as a determination sample.

Amplification of the cRNA can be performed by using a known method. A commercial kit for amplifying cRNA can be also used for the cRNA amplification. Here, the commercial kit includes, for example, trade name: One-Cycle Target Labeling and Control Reagents, manufactured by Affymetrix, Inc., and the like. In addition, the amplification of the cDNA can be performed by using a known method. A commercial kit for amplifying cDNA can be also used for the cDNA amplification. Purification of the mRNA can be performed by using a known purification method. In addition, a commercial kit may be also used for the mRNA purification.

Next, the expression level of each gene in the gene groups described in Table 1-1 and Table 1-2 is determined using the determination sample obtained in the step (B) [step (C)}].

In the step (C), for example, a microarray, quantitative RT-PCR, quantitative PCR, and the like can be used for determination of the expression level. Among them, it is preferable to use a microarray for determination, since the expression level can be rapidly and easily determined. In this case, the fluorescence intensity in the microarray may be directly used as the expression level in the following step. The determination of the expression level by a microarray can be performed by using a known method.

The expression level of each gene in the gene groups described in Table 1-1 and Table 1-2 can be determined by utilizing, for example, the nucleic acids (probe sets shown by Probe Set. ID) described in Table 1-1 and Table 1-2. In the examination method of the present invention, the nucleic acids (probe sets) described in Table 1-1 and Table 1-2 are used as a prognosis factor in the examination of prognosis of breast cancer. The nucleic acids (probe sets) are found by the present inventors as those having the great effects in the examination of prognosis of breast cancer in many cases. In addition, the number of the nucleic acids (probe sets) used in the prognosis factor in the examination method of the present invention is 95 and is considered as the number that gives the highest accuracy of the examination. Therefore, prognosis can be properly predicted for various cases according to the examination method of the present invention.

In the examination method of the present invention, when the expression level of each gene in the gene groups described in Table 1-1 and Table 1-2 is determined by using a microarray, for example, a microarray having at least the nucleic acids (probe sets) described in Table 1-1 and Table 1-2, and the like can be used as the microarray. The microarray includes, for example, trade name: Human Genome U133 Plus 2.0 Array, manufactured by Affymetrix, Inc., and the like. For example, when trade name: Human Genome U133 Plus 2.0 Array, manufactured by Affymetrix, Inc. described above is used, the expression level of each gene in the gene groups described in Table 1-1 and Table 1-2 can be determined at a time by the 95 nucleic acids (probe sets) shown by the Probe Set. ID described in Table 1-1 and Table 1-2.

Next, the expression level determined in the step (C) is analyzed [step (D)]. Thereafter, prognosis of breast cancer is examined, based on the analysis result obtained in the step (D) [step (E)].

In the step (D), the expression level can be analyzed by using, for example, a classification method, a hierarchical cluster analysis, and a scoring method. Here, as the expression level, one obtained by normalizing the determined raw data of the expression level, for example, by RMA algorithm, MAS5 algorithm, PLIER algorithm, or the like can be used. The RMA algorithm is available, for example, on the analysis software (manufactured by Affymetrix, Inc., trade name: Affymetrix Expression Console software).

As the classification method, a known method can be used. The classification method includes, for example, Between-group analysis (BGA) (see Culhane, A. C. et al., Bioinformatics, 2002, Vol. 18, pp. 1600-1608, "Between-group analysis of microarray data"), support vector machine (SVM), diagonal linear discriminant analysis (DLDA), k nearest neighbor classification (kNN), decision tree, Random Forest, neural net, and the like. Among them, BGA is preferable from the viewpoint of good classification of subjects into those predicted as good prognosis and those predicted as poor prognosis. In the case where the expression level is analyzed by using the classification method, those predicted as good prognosis and those predicted as poor prognosis based on the expression level are classified. Therefore, in this case, in the step (E), prognosis of breast cancer can be predicted according to the result of the classification. In the case where the BGA is used, a discriminant is constructed. Prognosis of breast cancer may be predicted based on solution D of discriminant.

The discriminant includes a discriminant represented by the following formula (1):

$$D = \frac{\sum_i w_i X_i}{\sum_i X_i} - 0.0061 \quad (1)$$

wherein "i" in the formula (1) shows the gene number provided to the nucleic acid described in Table 1-1 and Table 1-2, "$w_i$" in the formula (1) shows a weight coefficient corresponding to the nucleic acid with gene number i described in Table 1-1 and Table 1-2, "$X_i$" in the formula (1) shows a normalized expression level which is obtained by normalization using the following formula (2):

$$X_i = y_i + \text{abs}[\text{round}\{\min(y_{ij})-1\}] \quad (2)$$

and $$"\sum_i"$$

in the formula (1) shows the summation of each nucleic acid, and wherein "j" in the formula (2) shows the specimen number provided to each specimen, "$y_{ij}$" in the formula (2) shows the standardized expression level in a specimen with specimen number j of a gene corresponding to the nucleic acid with gene number i, "min" in the formula (2) shows the minimum value of the value in parentheses, "round" in the formula (2) shows the value obtained by rounding the value in parentheses to the nearest whole number, "abs" in the formula (2) shows the absolute value of the value in parentheses, and "$y_i$" in the formula (2) shows a standardized expression level of a gene corresponding to the nucleic acid with gene number i, the standardized expression level being obtained by standardization using the following formula (3):

$$y_i = x_i - u_i \quad (3)$$

wherein "$x_i$" in the formula (3) shows the expression level of a gene corresponding to the nucleic acid with gene number i, and "$u_i$" in the formula (3) shows the average value of specimens of the expression level of a gene corresponding to the nucleic acid with gene number i. In the case where the expression level is analyzed using the discriminant, the value of the expression level in the specimen is assigned to $x_i$ (i=1, 2, . . . , 95) of the discriminant in sequence, to calculate solution D. In this case, if solution D is a positive value, poor prognosis can be predicted, and if solution D is 0 or a negative value, good prognosis can be predicted, in the step (E).

The hierarchical cluster analysis can be performed by, for example, using the expression level data in a specimen collected from a subject (or data of fluorescence intensity associated with the expression level), the expression level data in a group of specimens which is already known as good prognosis (or data of fluorescence intensity associated with the expression level), and the expression level data in a group of specimens which is already known as poor prognosis (or data of fluorescence intensity associated with the expression level), to thereby calculate a distance showing the degree of similarity between specimens based on the expression level (or data of fluorescence intensity associated with the expression level), forming various clusters based on this distance, integrating the clusters, and creating a dendrogram. Here, the distance includes, for example, Spearman's rank correlation coefficient, Euclidean distance, and the like. In addition, the cluster integration can be performed by, for example, Ward's method, complete linkage method, centroid linkage method, or the like. Among them, by using Spearman's rank correlation coefficient and Ward's method, those predicted as good prognosis and those predicted as poor prognosis can be favorably classified. In this case, prognosis of breast cancer can be properly predicted according to the result of the hierarchical cluster analysis, in the step (E).

As the scoring method, a known method can be used. The scoring method includes, for example, principal component analysis, multiple regression analysis, logistic regression analysis, Partial Least Square, and the like. Among them, principal component analysis is preferable from the viewpoint of good classification of subjects into those predicted as good prognosis and those predicted as poor prognosis. In the case where the expression level is analyzed by using the scoring method, scoring is performed so as to classify into a score of a specimen predicted as good prognosis and a score of a specimen predicted as poor prognosis based on the expression level. Therefore, in this case, prognosis of breast cancer can be properly predicted according to the result of the scoring, in the step (E).

As described above, according to the method for examining prognosis of breast cancer of the present invention, since the expression level of each gene in the gene groups described in Table 1-1 and Table 1-2 is analyzed, prognosis of breast cancer can be properly examined.

By using the expression level of each gene in the gene groups described in Table 1-1 and Table 1-2, an indication for determining prognosis of breast cancer can be obtained and provided. The method for obtaining an indication for determining prognosis of breast cancer includes the steps of:

(a) extracting RNA from a specimen collected from a subject with breast cancer, (b) preparing a determination sample using the RNA extracted in the step (a), (c) determining the expression level of each gene in the gene groups described in Table 1-1 and Table 1-2 using the determination sample obtained in the step (b), (d) analyzing the expression level determined in the step (c), and (e) obtaining an indication for the possibility of poor prognosis or indication for the possibility of good prognosis of breast cancer of the subject, based on the analysis result obtained in the step (d). The steps (a) to (d) can be performed in the same manner as in the steps (A) to (D) in the method for examining prognosis of breast cancer. Also, an indication for the possibility of poor prognosis or indication for the possibility of good prognosis of breast cancer of the subject can be obtained in the step (e) by the method used in the step (E) in the method for examining prognosis of breast cancer.

EXAMPLES

Hereinbelow, the present invention will be described in detail with reference to Examples. However, the present invention is not limited to these Examples.

Example 1

Data of 549 cases were extracted from node-negative and ER-positive cases from 6 datasets including accession numbers: GSE2034, GSE2990, GSE4922, GSE6532, GSE7390, and GSE9195 in NCBI Gene Expression Omnibus of microarray experiments.

In each data of the 549 cases, the expression level of each nucleic acid (probe set) on the microarray used in the data acquisition was normalized for every dataset by using an RMA algorithm of the analysis software (manufactured by Affymetrix, Inc., trade name: Affymetrix Expression Console software). Next, the average expression level value of the nucleic acid in the dataset was subtracted from the expression level value of the nucleic acid (probe set) on the array used in the data acquisition, to standardize the expression level of the nucleic acid, for every dataset.

Thereafter, zScore was calculated for each of the nucleic acids (probe sets) on the array, by using a package "GeneMeta v1.16.0" contained in an additional package "BioConductor" ver. 2.4 used in software for statistical analysis "R", according to a literature by Jung Kyoon Choi et al., "Combining multiple microarray studies and modeling interstudy variation", Bioinformatics, Vol. 19, Suppl. 1, 2003, pp. i84-i90. Then, the nucleic acids (probe sets) were arranged in order of the absolute value of the zScore.

Next, a discriminant was constructed according to Between-group analysis. In order to obtain an optimal accuracy, the number of probe sets optimal for the examination of prognosis of breast cancer was obtained by Sequential Forward Filtering method. Here, while increasing the selected number of the nucleic acids (probe sets) by 5 until reaching to 300, from the nucleic acids (probe sets), in order of the absolute value of the zScore, the nucleic acids (probe sets) were selected to construct a discriminant.

Using each obtained discriminant and each data of the 549 cases, an examination accuracy of each discriminant was validated by Leave-One-Out Cross-Validation. The examination accuracy was evaluated by obtaining the sensitivity and specificity of each discriminant, creating an ROC curve based on the sensitivity and specificity, and calculating the area under the curve of this ROC curve. Moreover, a relationship between the area under the curve of the ROC curve and the number of the nucleic acids (probe sets) was examined, thereby obtaining the number (the optimal number) of the nucleic acids (probe sets) which maximizes the area under the curve of the ROC curve.

The sensitivity was obtained by dividing the number of specimens determined as "recurrence" (poor prognosis) for 10 years after surgery based on the observation result and predicted as having "recurrence" (poor prognosis) according to the discriminant, by the number of specimens determined as "recurrence" (poor prognosis) for 10 years after surgery based on the observation result, and multiplying by 100. In addition, the specificity was obtained by dividing the number of specimens determined as "no recurrence" (good prognosis) for 10 years after surgery based on the observation result and predicted as having "no recurrence" (good prognosis) according to the discriminant, by the number of specimens determined as "no recurrence" (good prognosis) based on the observation result, and multiplying by 100.

A graph showing the result of examining a relationship between the number of probes and the area under the curve of the ROC curve in Example 1 is shown in FIG. 1.

From the result shown in FIG. 1, it is found that the area under the curve of the ROC curve reaches the largest, when the number of nucleic acids (probe sets) is 95. From this result, it is found that the examination accuracy also reaches the highest when the number of nucleic acids (probe sets) is 95. These 95 nucleic acids (probe sets) are as shown in Table 1-1 and Table 1-2.

In addition, zScores, expression tendencies in the recurrent group having recurrence for 10 years after surgery, and weight coefficients in the discriminant of these 95 nucleic acids (probe sets) are shown in Table 2-1 and Table 2-2.

TABLE 2-1

| Gene Number | Probe Set. ID | BGA zScore | Expression Tendencies in Recurrent Group | Weight Coefficient |
|---|---|---|---|---|
| 1 | 219306_at | −5.3567 | increase | 0.5960 |
| 2 | 218585_s_at | −5.1377 | increase | 1.4097 |
| 3 | 221677_s_at | −5.0601 | increase | 0.4683 |
| 4 | 201088_at | −4.9734 | increase | 1.0480 |
| 5 | 209034_at | 4.9696 | decrease | −1.4059 |
| 6 | 202610_s_at | −4.9048 | increase | −0.0393 |
| 7 | 218906_x_at | −4.8323 | increase | 0.0880 |
| 8 | 212723_at | −4.6998 | increase | 0.3141 |
| 9 | 222231_s_at | −4.6324 | increase | 0.6264 |
| 10 | 208838_at | −4.6253 | increase | 0.2207 |
| 11 | 218039_at | −4.6029 | increase | 1.5846 |
| 12 | 209472_at | 4.6020 | decrease | −1.7235 |
| 13 | 212898_at | −4.5966 | increase | 0.1172 |
| 14 | 202620_s_at | −4.5827 | increase | 1.3605 |
| 15 | 201059_at | −4.5756 | increase | 0.3591 |
| 16 | 201841_s_at | −4.5605 | increase | 1.2420 |
| 17 | 203755_at | −4.5410 | increase | 0.9909 |
| 18 | 211750_x_at | −4.5346 | increase | 0.0145 |
| 19 | 38158_at | −4.5201 | increase | 0.5325 |
| 20 | 204709_s_at | −4.5107 | increase | 0.0798 |
| 21 | 201589_at | −4.4720 | increase | 0.3106 |
| 22 | 218460_at | −4.4386 | increase | 0.0198 |
| 23 | 207430_s_at | −4.4260 | increase | 1.9177 |
| 24 | 212139_at | −4.4166 | increase | −0.0501 |
| 25 | 211596_s_at | 4.4024 | decrease | −2.0999 |
| 26 | 212160_at | −4.4006 | increase | 0.3461 |
| 27 | 219238_at | 4.3966 | decrease | −1.2689 |
| 28 | 203432_at | −4.3549 | increase | 0.4665 |
| 29 | 201377_at | −4.3403 | increase | 0.1269 |
| 30 | 218875_s_at | −4.3334 | increase | 0.1012 |
| 31 | 221922_at | −4.3238 | increase | 0.4423 |
| 32 | 218727_at | −4.2747 | increase | −0.0411 |
| 33 | 207469_s_at | −4.2733 | increase | 0.8827 |
| 34 | 218483_s_at | 4.2641 | decrease | −1.3198 |
| 35 | 204641_at | −4.2552 | increase | 1.5825 |
| 36 | 219502_at | −4.2547 | increase | −0.1883 |
| 37 | 209054_s_at | −4.2423 | increase | 0.0465 |
| 38 | 220318_at | −4.2376 | increase | 0.3073 |
| 39 | 210297_s_at | −4.2337 | increase | 1.6681 |
| 40 | 209186_at | −4.2333 | increase | 0.2014 |
| 41 | 219787_s_at | −4.1833 | increase | 0.8181 |
| 42 | 45633_at | −4.1827 | increase | −0.2363 |
| 43 | 200848_at | 4.1800 | decrease | −1.5895 |

TABLE 2-1-continued

| Gene Number | Probe Set. ID | BGA zScore | Expression Tendencies in Recurrent Group | Weight Coefficient |
|---|---|---|---|---|
| 44 | 200822_x_at | −4.1767 | increase | 0.0814 |
| 45 | 211072_x_at | −4.1602 | increase | 0.0380 |
| 46 | 200811_at | 4.1591 | decrease | −1.4620 |
| 47 | 202864_s_at | 4.1381 | decrease | −1.3947 |
| 48 | 202154_x_at | −4.1334 | increase | 0.1241 |
| 49 | 213152_s_at | 4.1121 | decrease | −1.2495 |
| 50 | 209368_at | 4.0924 | decrease | −1.8835 |

TABLE 2-2

| 51 | 211058_x_at | −4.0877 | increase | 0.0646 |
|---|---|---|---|---|
| 52 | 209251_x_at | −4.0829 | increase | 0.0453 |
| 53 | 213646_x_at | −4.0808 | increase | 0.0396 |
| 54 | 204540_at | −4.0657 | increase | 1.8487 |
| 55 | 202026_at | 4.0646 | decrease | −1.3587 |
| 56 | 201090_x_at | −4.0595 | increase | 0.0733 |
| 57 | 213119_at | −4.0519 | increase | 0.0680 |
| 58 | 217840_at | −4.0419 | increase | 0.0313 |
| 59 | 206559_x_at | 4.0301 | decrease | −0.9727 |
| 60 | 202066_at | −4.0298 | increase | 0.7385 |
| 61 | 203108_at | −4.0225 | increase | 1.0799 |
| 62 | 218697_at | −4.0184 | increase | −0.0693 |
| 63 | 222039_at | −3.9873 | increase | 0.6820 |
| 64 | 202069_s_at | −3.9868 | increase | 0.2302 |
| 65 | 203362_s_at | −3.9840 | increase | 0.8095 |
| 66 | 202666_s_at | −3.9742 | increase | 0.2162 |
| 67 | 204892_x_at | 3.9593 | decrease | −0.9566 |
| 68 | 205682_x_at | 3.9520 | decrease | −1.0558 |
| 69 | 209714_s_at | −3.9454 | increase | 0.9594 |
| 70 | 218381_s_at | −3.9424 | increase | −0.0076 |
| 71 | 201947_s_at | −3.9400 | increase | 0.2632 |
| 72 | 212722_s_at | −3.9357 | increase | 0.0968 |
| 73 | 204825_at | −3.9323 | increase | 1.1379 |
| 74 | 203184_at | −3.9252 | increase | 0.7174 |
| 75 | 201266_at | −3.9251 | increase | 0.2610 |
| 76 | 202969_at | −3.9203 | increase | 0.2560 |
| 77 | 204817_at | −3.9002 | increase | 0.4866 |
| 78 | 209523_at | −3.9002 | increase | 0.3803 |
| 79 | 218491_s_at | 3.9000 | decrease | −1.3652 |
| 80 | 217363_x_at | 3.8939 | decrease | −0.9838 |
| 81 | 218009_s_at | −3.8933 | increase | 1.6691 |
| 82 | 204026_s_at | −3.8818 | increase | 0.9942 |
| 83 | 218355_at | −3.8817 | increase | 1.1017 |
| 84 | 202153_s_at | −3.8766 | increase | −0.0983 |
| 85 | 213011_s_at | −3.8763 | increase | 0.1005 |
| 86 | 217966_s_at | 3.8759 | decrease | −2.4459 |
| 87 | 214782_at | −3.8666 | increase | 0.2306 |
| 88 | 217967_s_at | 3.8652 | decrease | −2.7067 |
| 89 | 204649_at | −3.8617 | increase | 0.1495 |
| 90 | 35671_at | −3.8585 | increase | 0.0169 |
| 91 | 213502_x_at | 3.8571 | decrease | −2.1336 |
| 92 | 221285_at | 3.8490 | decrease | −0.9209 |
| 93 | 221519_at | 3.8432 | decrease | −1.1897 |
| 94 | 202551_s_at | 3.8420 | decrease | −2.0141 |
| 95 | 217138_x_at | 3.8260 | decrease | −1.0505 |

Based on the above result, the conclusive discriminant was constructed. The constructed discriminant is a discriminant represented by the following formula (1):

$$D = \frac{\sum_i w_i \times X_i}{\sum_i X_i} - 0.0061 \quad (1)$$

{in the formula (1), "i" shows the gene number provided to the nucleic acid described in Table 1-1 and Table 1-2, "$w_i$" shows a weight coefficient corresponding to the nucleic acid with gene number i described in Table 1-1 and Table 1-2, and "$X_i$" shows a normalized expression level which is obtained by normalization using the following formula (2):

$$X_i = y_i + \text{abs}[\text{round}\{\min(y_{ij}) - 1\}] \quad (2)$$

[in the formula (2), "j" shows the specimen number provided to each specimen, "$y_{ij}$" shows the standardized expression level in a specimen with specimen number j of a gene corresponding to the nucleic acid with gene number i, "min" shows the minimum value of the value in parentheses, "round" shows the value obtained by rounding the value in parentheses to the nearest whole number, "abs" shows the absolute value of the value in parentheses, "$y_i$" shows a standardized expression level of a gene corresponding to the nucleic acid with gene number i, the standardized expression level being obtained by standardization using the following formula (3):

$$y_i = x_i - u_i \quad (3)$$

(in the formula (3), "$x_i$" shows the expression level of a gene corresponding to the nucleic acid with gene number i, and "$u_i$" shows the average value of specimens of the expression level of a gene corresponding to the nucleic acid with gene number) i.).]

and $\Sigma_i$ shows the summation of each nucleic acid.}.

Here, poor prognosis is predicted when solution D of the discriminant is a positive value, and good prognosis is predicted when solution D is 0 or a negative value.

Example 2

(1) Data Acquisition of Expression Level of Nucleic Acids (Probe Sets)

RNA was extracted from tumor tissues obtained at each surgery of 105 breast cancer patients by using an RNA extraction kit (manufactured by QIAGEN Sciences, trade name: Qiagen RNeasy mini kit).

The 105 breast cancer patients are node-negative and ER-positive patients who underwent breast conserving surgery followed by radiation therapy or mastectomy during the period 1996-2005. The age range of these patients is 30 to 83, and the median age is 54. Clinicopathological features of the 105 breast cancer patients are shown in Table 3.

TABLE 3

| | | Number of patients among 105 patients | Prediction by 95-gene classifier | | p-value |
|---|---|---|---|---|---|
| | | | low-risk group for recurrence (good prognosis) | high-risk group for recurrence (poor prognosis) | |
| Postmenopausal | | 56 | 37 | 19 | 0.10 |
| Tumor size T | T = 1 | 58 | 37 | 21 | 0.20 |

TABLE 3-continued

|  |  | Number of patients among 105 patients | Prediction by 95-gene classifier | | p-value |
| --- | --- | --- | --- | --- | --- |
|  |  |  | low-risk group for recurrence (good prognosis) | high-risk group for recurrence (poor prognosis) |  |
|  | T = 2 | 45 | 23 | 22 |  |
|  | T = 3 | 2 | 1 | 1 |  |
|  | T = 4 | 0 | 0 | 0 |  |
| Histological Grade | 1 | 29 | 22 | 7 | <0.01 |
|  | 2 | 62 | 36 | 26 |  |
|  | 3 | 14 | 3 | 11 |  |
| Presence or absence of ER | positive | 105 | 61 | 44 |  |
|  | negative | 0 | 0 | 0 |  |
| Presence or absence of PR | positive | 87 | 52 | 35 | 0.45 |
|  | negative | 18 | 9 | 9 |  |
| Presence or absence of HER2 | positive | 19 | 8 | 11 | 0.12 |
|  | negative | 86 | 53 | 33 |  |
| Ki67 | positive | 19 | 7 | 12 | 0.04 |
|  | negative | 86 | 54 | 32 |  |

The tumor size T is represented by four levels, 1 to 4, based on the determination result by diagnostic imaging such as mammography and ultrasound. Here, T=1 shows that the maximum size of the tumor is 2 cm or less, T=2 shows that the maximum size of the tumor is more than 2 cm and 5 cm or less, T=3 shows that the maximum size of the tumor is more than 5 cm, and T=4 shows that the tumor invades the chest wall or skin, regardless of the tumor size.

The histological grade is represented by three levels, 1 to 3, based on the total score of the score of the nuclear grade (Score 1: low frequency of nuclear pleomorphism, Score 2: moderate frequency of nuclear pleomorphism, Score 3: high frequency of nuclear pleomorphism), the score of the change rate of tissue structure (Score 1: <10%, Score 2: 10 to 75%, Score 3: >75%), and the score of the frequency of cell division (Score 1: 0-4 mitoses per 10 high power field (HPF), Score 2: 5-10 mitoses per 10 HPF, Score 3: 11≤mitoses per 10 high power field (HPF)). Here, conventionally, it has been considered that HG=1 has been Score 3 to 5 and has shown cancer with good prognosis, that HG=2 has been Score 6 to 7, and that HG=3 has been Score 8 to 9 and has shown cancer with the worst prognosis.

The presence or absence of ER is represented by positive and negative, based on the result of the immunostaining method. Conventionally, it has been generally considered that prognosis has been poor in the case of ER negative, and that prognosis has been good in the case of ER positive.

The presence or absence of PR is represented by positive and negative, based on the result of the immunostaining method. Conventionally, it has been generally considered that prognosis has been poor in the case of PR negative, and that prognosis has been good in the case of PR positive.

The presence or absence of HER2 is represented by positive and negative, based on the result of the immunostaining method. Conventionally, it has been is generally considered that prognosis has been poor in the case of HER2 positive, and that prognosis has been good in the case of HER2 negative.

The Ki67 is represented by positive and negative, based on the result of the immunostaining method. Conventionally, it has been generally considered that prognosis has been poor in the case of Ki67 positive, and that prognosis has been good in the case of Ki67 negative.

Next, cRNA was amplified, biotinylated, and fragmented, using 1 μg of the obtained RNA [RNA Integrity Number (RIN) value >6] and a kit for expression analysis (manufactured by Affymetrix, Inc., trade name: One-Cycle Target Labeling and Control Reagents).

The obtained fragmented biotin-labeled cRNA was hybridized over night with the nucleic acids (probe sets) on a human genome array for expression analysis (manufactured by Affymetrix, Inc., trade name: Human Genome U133 Plus 2.0 Array). Hybridization of the fragmented biotin-labeled cRNA with the nucleic acids (probe sets) on the array was performed according to the recommended conditions of the manufacturer (Affymetrix, Inc.).

Next, the array after hybridization was subjected to a machine specialized for wash and stain operation of microarrays (manufactured by Affymetrix, Inc., trade name: GeneChip Fluidics Station 450), thereby performing fluorescent staining of the cRNA hybridized with the nucleic acids (probe, sets) on the array and washing.

Thereafter, the array was subjected to a laser scanner [manufactured by Affymetrix, Inc., trade name: GeneChip (registered trademark) Scanner 3000], thereby reading a signal based on the fluorescently-labeled substance of the cRNA hybridized with the nucleic acids (probe sets) on the array was read, and quantifing the fluorescent intensity.

The obtained fluorescent intensity data was processed by a software [manufactured by Affymetrix, Inc., trade name: GeneChip (registered trademark) Operating Software], to obtain a CEL file.

The expression level data (fluorescent intensity data) of the nucleic acids (probe sets) in all 105 cases of breast cancer patients was normalized by using the obtained 105 cases of CEL file data and the RMA algorithm of the analysis software (manufactured by Affymetrix, Inc., trade name: Affymetrix Expression Console software).

(2) Validation of Performance of Discriminant

Next, whether all 105 cases of breast cancer patients would cause a recurrence was predicted by using the data after normalization obtained in the above (1) and the discriminant. Moreover, assuming the pathological observation result as the true value, the performance of the discriminant was evaluated by comparing the pathological observation result with the result predicted by the discriminant. The result of examining a relationship between the result predicted by the discriminant and the observation result for the 105 cases of breast cancer patients in Example 2 is shown in FIG. 2.

From the result shown in FIG. 2, it is found that, among all 105 cases, 61 cases of breast cancer patients were predicted as having "no recurrence," and 44 cases of breast cancer patients were predicted as having "recurrence". In other words, in the case where the discriminant is used, it is found that, for the 61 cases of breast cancer patients, good prognosis is predicted, and for the 44 cases of breast cancer patients, poor prognosis is predicted.

In addition, when the performance of the discriminant is evaluated assuming the pathological observation result as the true value, it is found that the sensitivity, specificity, negative predictive value (NPV), and positive predictive value (PPV) are 83.3%, 70.4%, 93.4%, and 45.5%, respectively.

Therefore, from these results, it is suggested that prognosis of breast cancer can be properly predicted by using the expression level of each gene in the gene groups described in Table 1-1 and Table 1-2 and the discriminant.

In addition, the breast cancer patients predicted as having "no recurrence" according to the discriminant (low-risk group for recurrence) and the breast cancer patients predicted as having "recurrence" according to the discriminant (high-risk group for recurrence) were each observed after surgery. The recurrence-free survival rate was examined by Kaplan-Meier plot. In addition, the result was evaluated by the log-rank test. A relationship between the period after surgery and the recurrence-free survival rate in Example 2 is shown in FIG. 3.

Figure 3:
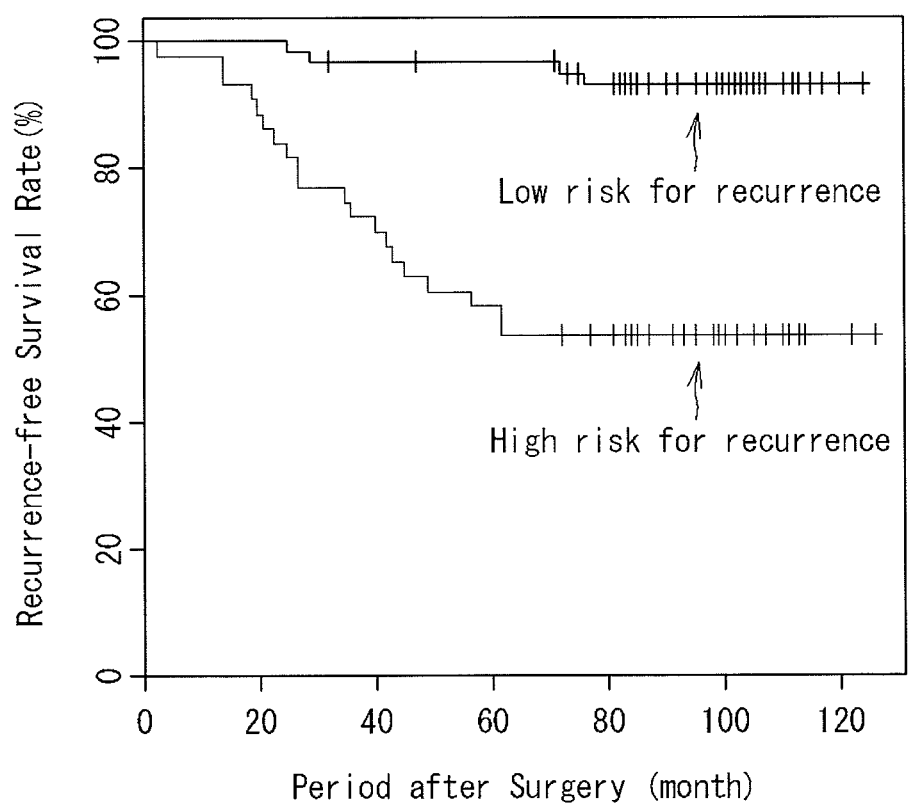
FIG. 3 is a graph showing the result of examining a relationship between the period after surgery and the recurrence-free survival rate in Example 2.

From the result shown in FIG. 3, it is found that, while the 10-year recurrence-free survival rates after surgery are 53% in the high-risk group for recurrence (in the figure, "high-risk for recurrence") and 93% in the low-risk group for recurrence (in the figure, "low-risk for recurrence"). In addition, since the log-rank test resulted in $p=8.6\times10^{-7}$, it is found that the low-risk group for recurrence shows significantly better prognosis than the high-risk group for recurrence.

Therefore, from these results, it is found that prognosis of breast cancer can be properly predicted with a high accuracy by using the expression level of the nucleic acids (probe sets) described in Table 1-1 and Table 1-2 and the discriminant.

Test Example 1

For each of an examination method using the 95 nucleic acids as a prognosis factor (Experimental Number 1), an examination method using patient's menopausal status as a prognosis factor (Experimental Number 2), an examination method using the tumor size as a prognosis factor (Experimental Number 3), an examination method using histological grade as a prognosis factor (Experimental Number 4), an examination method using the presence or absence of PR as a prognosis factor (Experimental Number 5), an examination method using the presence or absence of human epidermal growth factor receptor 2 (HER2) as a prognosis factor (Experimental Number 6), an examination method using whether the ratio of Ki67 positive cells in all cells is 20% or more as a prognosis factor (Experimental Number 7), and an examination method by Genomic Grade Index (GGI) using 97 genes that are different type from the 95 genes as a prognosis factor (Experimental Number 8), multivariate COX regression hazard analysis was performed by using an additional package "survival v2.35-4" used in a software for statistical analysis "R". The GGI was obtained according to a literature of Sotiriou Christos et al. (Journal of the National Cancer Institute, 2006, Vol. 98, Issue 4, pp. 262-272).

The result is shown in Table 4. In the table, "95genes" shows the examination method using the 95 nucleic acids as a prognosis factor (Experimental Number 1), "Mens" being the examination method using patient's menopausal status as a prognosis factor (Experimental Number 2), "T" being the examination method using the tumor size as a prognosis factor (Experimental Number 3), "HG" being the examination method using histological grade as a prognosis factor (Experimental Number 4), "PgR" being the examination method using the presence or absence of PR as a prognosis factor (Experimental Number 5), "HER2" being the examination method using the presence or absence of HER2 as a prognosis factor (Experimental Number 6), "Ki67" being the examination method using whether the ratio of Ki67 positive cells in all cells is 20% or more as a prognosis factor (Experimental Number 7), and "sign.GGI" being the examination method by GGI using 97 genes that are different type from the 95 genes as a prognosis factor (Experimental Number 8). Each hazard ratio is the value calculated assuming the hazard in the case of falling under "reference" in the table as 1.0. The menopausal status is represented as premenopausal and postmenopausal. In addition, conventionally, prognosis is considered to be good when sign.GGI is low, and prognosis is considered to be poor when sign.GGI is high.

TABLE 4

| Experimental | Prognosis | | Multivariate Analysis | |
|---|---|---|---|---|
| Number | Factor | Reference | Hazard Ratio | p-value |
| 1 | 95genes | no recurrence | 7.70 | 9.6E−04 ** |
| 2 | Mens | premenopausal | 1.32 | 0.5345 |
| 3 | T | T = 1 | 2.25 | 0.0275 * |
| 4 | HG | HG = 1, 2 | 1.24 | 0.7046 |
| 5 | PgR | negative | 0.56 | 0.2654 |
| 6 | HER2 | negative | 2.21 | 0.0911 |
| 7 | ki67 | negative | 0.65 | 0.4288 |
| 8 | sign.GGI | low | 1.08 | 0.7796 |

* 5% significant
** 1% significant

From the result shown in Table 4, it is found that the examination method of the present invention is an examination method with a high accuracy as compared with other examination methods, since the examination method using the discriminant in which the 95 nucleic acids are used as a prognosis factor (Experimental Number 1; the examination method of the present invention) has a hazard ratio of 7.70 and a p-value of 9.6E-04.

Example 3

Figure 4:
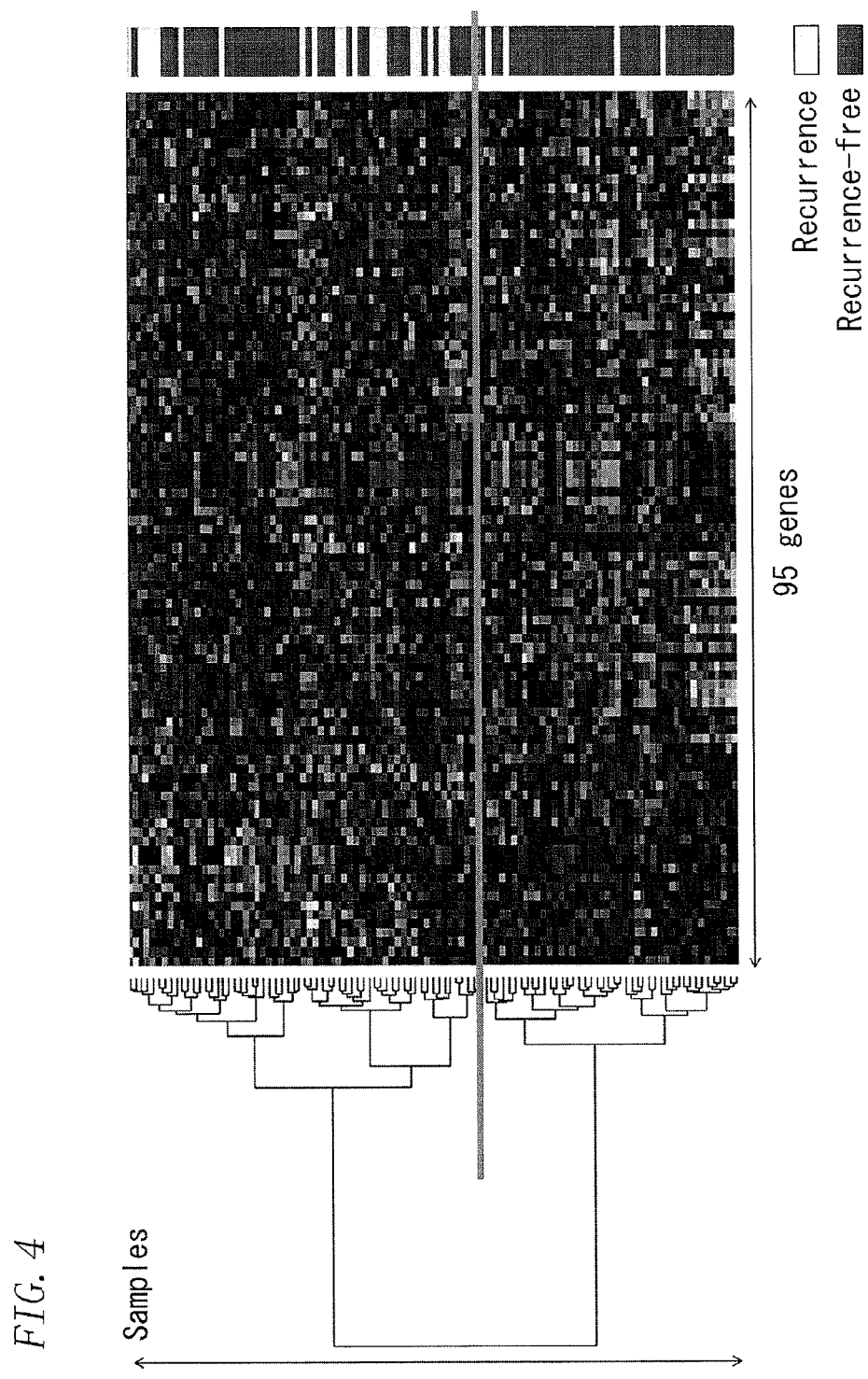
FIG. 4 is a dendrogram showing the result of performing a hierarchical cluster analysis of the expression level data of genes corresponding to the nucleic acids (probe sets) in each of 105 cases of breast cancer patients in Example 3.

For the data after normalization obtained in (1) of Example 2, a hierarchical cluster analysis was performed using Spearman's rank correlation coefficient and Ward's method, to create a dendrogram. The result of performing a hierarchical cluster analysis of the expression level data of the nucleic acids (probe sets) in each of 105 cases of breast cancer patients in Example 3 is shown in FIG. 4. In FIG. 4, a heat map representing the expression level of the nucleic acids (probe sets) is shown in the left, and the determination result of recurrence for 10 years after surgery (in the figure, "recurrence") and no recurrence for 10 years after surgery (in the figure, "recurrence-free") by the observation result is shown in the right.

From the result shown in FIG. 4, it is found that the breast cancer patients determined as recurrence (poor prognosis) for 10 years after surgery by the observation result (many in the upper part) and the breast cancer patients determined as no recurrence (good prognosis) for 10 years after surgery by the observation result (many in the lower part) can be classified, with a bold line drawn so as to divide the dendrogram serving as a boundary. Therefore, from these results, it is found that prognosis of breast cancer can be predicted with a high accuracy, and that prognosis of breast cancer can be properly examined by performing a hierarchical cluster analysis with the expression level of each gene in the gene groups described in Table 1-1 and Table 1-2.

Example 4

Figure 5:
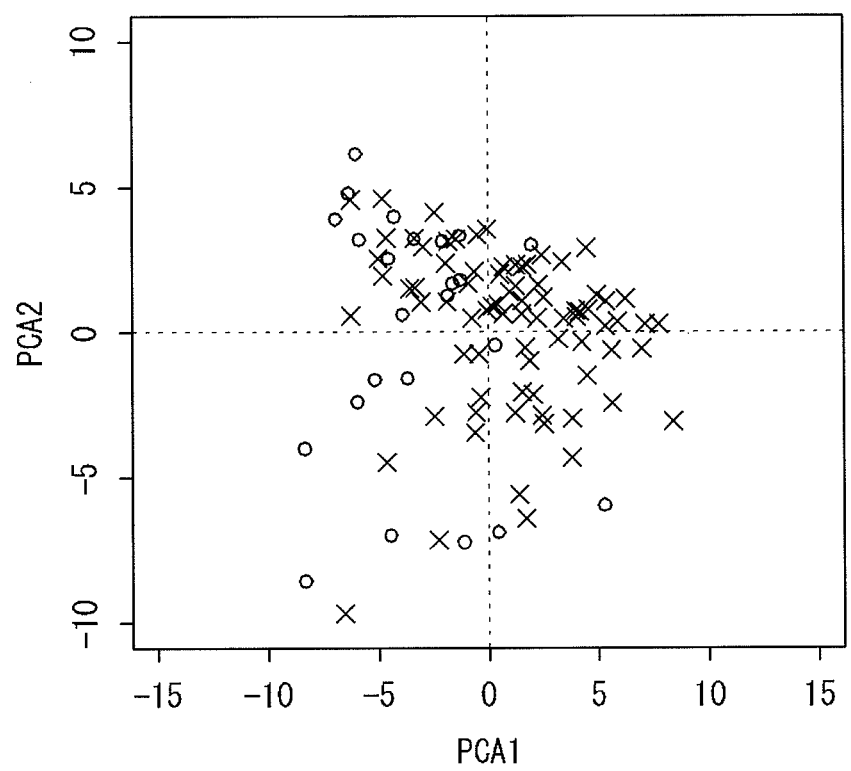
FIG. 5 is a scatter plot of the first principal component score and the second principal component score calculated based on the expression level data of each of 105 cases of breast cancer patients in Example 4.

For the data after normalization obtained in (1) of Example 2, principal component analysis was performed by using the genes described in Table 1-1 and Table 1-2, to calculate a conversion coefficient of each gene. In addition, the first and second principal component scores were calculated. The conversion coefficients calculated in Example 4 are shown in Table 5-1 and Table 5-2. In addition, a scatter plot of the first principal component score and the second principal component score calculated based on the expression level data of each of 105 cases of breast cancer patients in Example 4 is shown in FIG. 5. In FIG. 5, "PCA1" shows the first principal component score, and "PCA2" shows the second principal component score. In the figure, open circles are the breast cancer patients determined as "recurrence" for 10 years after surgery based on the observation result, and crosses are the breast cancer patients determined as "no recurrence" for 10 years after surgery based on the observation result.

TABLE 5-1

| Gene Number | Probe Set. ID | Conversion Coefficient in First Principal Component | Conversion Coefficient in Second Principal Component |
|---|---|---|---|
| 1 | 219306_at | −0.1316 | 0.0596 |
| 2 | 218585_s_at | −0.2082 | 0.0956 |
| 3 | 221677_s_at | −0.1003 | 0.0528 |
| 4 | 201088_at | −0.1770 | 0.0207 |
| 5 | 209034_at | 0.0568 | 0.0142 |
| 6 | 202610_s_at | −0.0333 | 0.0120 |
| 7 | 218906_x_at | −0.0339 | −0.0056 |
| 8 | 212723_at | −0.0831 | −0.0100 |
| 9 | 222231_s_at | −0.0986 | −0.0266 |
| 10 | 208838_at | −0.0603 | −0.0105 |
| 11 | 218039_at | −0.2359 | 0.0856 |
| 12 | 209472_at | 0.0395 | −0.0048 |
| 13 | 212898_at | −0.0518 | −0.0014 |
| 14 | 202620_s_at | −0.1275 | 0.1119 |
| 15 | 201059_at | −0.0494 | −0.0264 |
| 16 | 201841_s_at | −0.1071 | −0.0930 |
| 17 | 203755_at | −0.1917 | 0.0860 |
| 18 | 211750_x_at | −0.0606 | 0.0188 |
| 19 | 38158_at | −0.1045 | 0.0345 |
| 20 | 204709_s_at | −0.1103 | 0.0549 |
| 21 | 201589_at | −0.0860 | 0.0098 |
| 22 | 218460_at | −0.0214 | −0.0057 |
| 23 | 207430_s_at | −0.2134 | −0.6702 |
| 24 | 212139_at | −0.0356 | −0.0072 |
| 25 | 211596_s_at | 0.1028 | −0.0321 |
| 26 | 212160_at | −0.1002 | 0.0415 |
| 27 | 219238_at | 0.0325 | −0.0196 |
| 28 | 203432_at | −0.1295 | 0.0264 |
| 29 | 201377_at | −0.0446 | 0.0259 |
| 30 | 218875_s_at | −0.0859 | 0.0387 |
| 31 | 221922_at | −0.1019 | 0.0721 |
| 32 | 218727_at | −0.0210 | 0.0092 |
| 33 | 207469_s_at | −0.1364 | 0.0176 |
| 34 | 218483_s_at | 0.0522 | −0.0110 |
| 35 | 204641_at | −0.2144 | 0.1173 |
| 36 | 219502_at | −0.0497 | 0.0123 |
| 37 | 209054_s_at | −0.0536 | 0.0045 |
| 38 | 220318_at | −0.0752 | −0.0135 |
| 39 | 210297_s_at | −0.1929 | −0.6064 |
| 40 | 209186_at | −0.0511 | 0.0198 |
| 41 | 219787_s_at | −0.1676 | 0.0745 |

TABLE 5-1-continued

| Gene Number | Probe Set. ID | Conversion Coefficient in First Principal Component | Conversion Coefficient in Second Principal Component |
|---|---|---|---|
| 42 | 45633_at | −0.0476 | −0.0005 |
| 43 | 200848_at | 0.0460 | 0.0000 |
| 44 | 200822_x_at | −0.0596 | 0.0307 |
| 45 | 211072_x_at | −0.0630 | 0.0205 |
| 46 | 200811_at | 0.0714 | −0.0371 |
| 47 | 202864_s_at | 0.0152 | 0.0097 |
| 48 | 202154_x_at | −0.0484 | 0.0101 |
| 49 | 213152_s_at | 0.0489 | 0.0090 |
| 50 | 209368_at | 0.1107 | −0.0240 |

TABLE 5-2

| Gene Number | Probe Set. ID | Conversion Coefficient in First Principal Component | Conversion Coefficient in Second Principal Component |
|---|---|---|---|
| 51 | 211058_x_at | −0.0613 | 0.0181 |
| 52 | 209251_x_at | −0.0599 | 0.0193 |
| 53 | 213646_x_at | −0.0602 | 0.0204 |
| 54 | 204540_at | −0.1123 | −0.1300 |
| 55 | 202026_at | 0.0280 | 0.0288 |
| 56 | 201090_x_at | −0.0636 | 0.0220 |
| 57 | 213119_at | −0.0271 | 0.0071 |
| 58 | 217840_at | −0.0341 | −0.0169 |
| 59 | 206559_x_at | 0.0283 | −0.0050 |
| 60 | 202066_at | −0.0868 | −0.0215 |
| 61 | 203108_at | −0.0801 | −0.1074 |
| 62 | 218697_at | −0.0095 | −0.0034 |
| 63 | 222039_at | −0.1277 | 0.0404 |
| 64 | 202069_s_at | −0.0669 | 0.0043 |
| 65 | 203362_s_at | −0.2108 | 0.0775 |
| 66 | 202666_s_at | −0.0790 | 0.0103 |
| 67 | 204892_x_at | 0.0297 | −0.0038 |
| 68 | 205682_x_at | 0.0261 | 0.0025 |
| 69 | 209714_s_at | −0.1942 | 0.0663 |
| 70 | 218381_s_at | −0.0337 | 0.0084 |
| 71 | 201947_s_at | −0.0800 | −0.0273 |
| 72 | 212722_s_at | −0.0688 | −0.0040 |
| 73 | 204825_at | −0.1787 | 0.0849 |
| 74 | 203184_at | −0.0520 | −0.0363 |
| 75 | 201266_at | −0.0772 | 0.0104 |
| 76 | 202969_at | −0.0490 | 0.0042 |
| 77 | 204817_at | −0.1072 | 0.0286 |
| 78 | 209523_at | −0.0977 | 0.0404 |
| 79 | 218491_s_at | 0.0594 | −0.0088 |
| 80 | 217363_x_at | 0.0168 | 0.0061 |
| 81 | 218009_s_at | −0.2386 | 0.0817 |
| 82 | 204026_s_at | −0.1952 | 0.0760 |
| 83 | 218355_at | −0.1904 | 0.0697 |
| 84 | 202153_s_at | −0.0384 | 0.0261 |
| 85 | 213011_s_at | −0.0634 | 0.0331 |
| 86 | 217966_s_at | 0.0966 | −0.0543 |
| 87 | 214782_at | −0.0334 | −0.0120 |
| 88 | 217967_s_at | 0.1200 | −0.0865 |
| 89 | 204649_at | −0.0783 | 0.0241 |
| 90 | 35671_at | −0.0225 | −0.0215 |
| 91 | 213502_x_at | 0.0521 | 0.0383 |
| 92 | 221285_at | 0.0076 | −0.0023 |
| 93 | 221519_at | 0.0428 | −0.0122 |
| 94 | 202551_s_at | 0.1254 | −0.0316 |
| 95 | 217138_x_at | 0.0165 | 0.0017 |
| Constant Term | | −1.2329E−17 | −9.3129E−17 |

From the result shown in FIG. 5, it is found that the breast cancer patients determined as "no recurrence" (good prognosis) for 10 years after surgery based on the observation result and the breast cancer patients determined as "recurrence" (poor prognosis) for 10 years after surgery based on the observation result can be classified, with a point in the horizontal axis where the first principal component score is 0 serving as a boundary.

Therefore, from these results, it is found that prognosis of breast cancer can be predicted with a high accuracy, and prognosis of breast cancer can be properly examined by performing principal component analysis using the expression level of each gene in the gene groups described in Table 1-1 and Table 1-2.

The present invention can be embodiment in any other forms without departing from the spirit or essential characteristics of the invention. Therefore, the above-described examples are merely illustration in all aspects, and should not be understood to be limited thereto. The scope of the present invention is given in the claims, and is not bound to the description of the specification. Further, all modifications and changes belonging to the scope of equivalency of the claims are intended to be embraced within the scope of the present invention.

CITATION LIST

Patent Literature

Published Japanese Translation of PCT International Publication for Patent Application No. 2009-131262
Publication of Unexamined Patent Application No. 2007-528218

Non Patent Literature

Sotiriou Christos et al., "Gene expression profiling in breast cancer: understanding the molecular basis of histologic grade to improve prognosis.", Journal of the National Cancer Institute, published on Feb. 15, 2006, Vol. 98, Issue 4, pp. 262-272

The invention claimed is:

1. A method for examining prognosis of breast cancer comprising the steps of:
(A) extracting RNA from a specimen collected from a subject,
(B) preparing a determination sample using the RNA extracted in the step (A),
(C) determining the expression level of each gene in the gene groups described in Table 1-1-1 and Table 1-2-1 using the determination sample obtained in the step (B),
(D) analyzing the expression level of each gene determined in the step (C) comprising calculating solution D of a discriminant using the expression level and the discriminant is represented by the following formula (1):

$$D = \frac{\sum_i w_i \times X_i}{\sum_i X_i} - 0.0061, \quad (1)$$

(E) examining prognosis of breast cancer, based on the analysis result obtained in the step (D), and predicting a poor prognosis when the solution D of the discriminant is a positive value, and a good prognosis when the solution D is 0 or a negative value,
wherein i in the formula (1) shows a gene number provided to the nucleic acid described in Table 1-1 and Table 1-2, $w_i$ in the formula (1) shows a weight coefficient corresponding to the nucleic acid with gene number i described in Table 1-1 and Table 1-2, and $X_i$ in the formula (1) shows a normalized expression level which is obtained by normalization using the following formula (2):

$$X_i = y_i + \text{abs}[\text{round}\{\min(y_{ij})-1\}] \quad (2)$$

and $\Sigma_i$ in the formula (1) shows the summation of each nucleic acid, and wherein j in the formula (2) shows the specimen number provided to each specimen, $y_{ij}$ in the formula (2) shows the standardized expression level in a specimen with specimen number j of a gene corresponding to the nucleic acid with gene number i, min in the formula (2) shows the minimum value of the value in parentheses, round in the formula (2) shows the value obtained by rounding the value in parentheses to the nearest whole number, abs in the formula (2) shows the absolute value of the value in parentheses, and $y_i$ in the formula (2) shows a standardized expression level of a gene corresponding to the nucleic acid with gene number i, the standardized expression level being obtained by standardization using the following formula (3):

$$y_i = x_i - u_i \quad (3)$$

wherein $x_i$ in the formula (3) shows the expression level of a gene corresponding to the nucleic acid with gene number i, and $u_i$ in the formula (3) shows the average value of specimens of the expression level of a gene corresponding to the nucleic acid with gene number I, wherein Table 1-1-1 and Table 1-2-1 are:

TABLE 1-1-1

| Gene Number | Probe Set. ID | Gene Symbol | UniGene.ID | GenBank Accession Number |
|---|---|---|---|---|
| 1 | 219306_at | KIF15 | Hs.646856 | NM_020242 |
| 2 | 218585_s_at | DTL | Hs.656473 | NM_016448 |
| 3 | 221677_s_at | DONSON | Hs.436341 | AF232674 |
| 4 | 201088_at | KPNA2 | Hs.594238 | NM_002266 |
| 5 | 209034_at | PNRC1 | Hs.75969 | AF279899 |
| 6 | 202610_s_at | MED14 | Hs.407604 | AF135802 |
| 7 | 218906_x_at | KLC2 | Hs.280792 | NM_022822 |
| 8 | 212723_at | JMJD6 | Hs.514505 | AK021780 |
| 9 | 222231_s_at | LRRC59 | Hs.370927 | AK025328 |
| 10 | 208838_at | CAND1 | Hs.546407 | AB020636 |
| 11 | 218039_at | NUSAP1 | Hs.615092 | NM_016359 |
| 12 | 209472_at | CCBL2 | Hs.481898 | BC000819 |
| 13 | 212898_at | KIAA0406 | Hs.655481 | AB007866 |
| 14 | 202620_s_at | PLOD2 | Hs.477866 | NM_000935 |
| 15 | 201059_at | CTTN | Hs.596164 | NM_005231 |
| 16 | 201841_s_at | HSPB1 | Hs.520973 | NM_001540 |
| 17 | 203755_at | BUB1B | Hs.631699 | NM_001211 |
| 18 | 211750_x_at | TUBA1C | Hs.719091 | BC005946 |
| 19 | 38158_at | ESPL1 | Hs.153479 | D79987 |
| 20 | 204709_s_at | KIF23 | Hs.270845 | NM_004856 |
| 21 | 201589_at | SMC1A | Hs.211602 | D80000 |
| 22 | 218460_at | HEATR2 | Hs.535896 | NM_017802 |
| 23 | 207430_s_at | MSMB | Hs.255462 | NM_002443 |
| 24 | 212139_at | GCN1L1 | Hs.298716 | D86973 |
| 25 | 211596_s_at | LRIG1 | Hs.518055 | AB050468 |
| 26 | 212160_at | XPOT | Hs.85951 | AI984005 |
| 27 | 219238_at | PIGV | Hs.259605 | NM_017837 |
| 28 | 203432_at | TMPO | Hs.11355 | AW272611 |
| 29 | 201377_at | UBAP2L | Hs.490551 | NM_014847 |
| 30 | 218875_s_at | FBXO5 | Hs.520506 | NM_012177 |
| 31 | 221922_at | GPSM2 | Hs.584901 | AW195581 |
| 32 | 218727_at | SLC38A7 | Hs.10499 | NM_018231 |
| 33 | 207469_s_at | PIR | Hs.495728 | NM_003662 |
| 34 | 218483_s_at | C11orf60 | Hs.533738 | NM_020153 |
| 35 | 204641_at | NEK2 | Hs.153704 | NM_002497 |
| 36 | 219502_at | NEIL3 | Hs.405467 | NM_018248 |
| 37 | 209054_s_at | WHSC1 | Hs.113876 | AF083389 |
| 38 | 220318_at | EPN3 | Hs.670090 | NM_017957 |
| 39 | 210297_s_at | MSMB | Hs.255462 | U22178 |
| 40 | 209186_at | ATP2A2 | Hs.506759 | M23114 |
| 41 | 219787_s_at | ECT2 | Hs.518299 | NM_018098 |
| 42 | 45633_at | GINS3 | Hs.47125 | AI421812 |
| 43 | 200848_at | AHCYL1 | Hs.705418 | AA479488 |
| 44 | 200822_x_at | TPI1 | Hs.524219 | NM_000365 |

TABLE 1-1-1-continued

| Gene Number | Probe Set. ID | Gene Symbol | UniGene.ID | GenBank Accession Number |
|---|---|---|---|---|
| 45 | 211072_x_at | TUBA1B | Hs.719075 | BC006481 |
| 46 | 200811_at | CIRBP | Hs.634522 | NM_001280 |
| 47 | 202864_s_at | SP100 | Hs.369056 | NM_003113 |
| 48 | 202154_x_at | TUBB3 | Hs.511743 | NM_006086 |
| 49 | 213152_s_at | SFRS2B | Hs.476680 | AI343248 |
| 50 | 209368_at | EPHX2 | Hs.212088 | AF233336 |

TABLE 1-2-1

| Gene Number | Probe Set. ID | Gene Symbol | UniGene.ID | GenBank Accession Number |
|---|---|---|---|---|
| 51 | 211058_x_at | TUBA1B | Hs.719075 | BC006379 |
| 52 | 209251_x_at | TUBA1C | Hs.719091 | BC004949 |
| 53 | 213646_x_at | TUBA1B | Hs.719075 | BE300252 |
| 54 | 204540_at | EEF1A2 | Hs.433839 | NM_001958 |
| 55 | 202026_at | SDHD | Hs.719164 | NM_003002 |
| 56 | 201090_x_at | TUBA1B | Hs.719075 | NM_006082 |
| 57 | 213119_at | SLC36A1 | Hs.269004 | AW058600 |
| 58 | 217840_at | DDX41 | Hs.484288 | NM_016222 |
| 59 | 206559_x_at | EEF1A1 | — | NM_001403 |
| 60 | 202066_at | PPF1A1 | Hs.530749 | AA195259 |
| 61 | 203108_at | GPRC5A | Hs.631733 | NM_003979 |
| 62 | 218697_at | NCKIPSD | Hs.655006 | NM_016453 |
| 63 | 222039_at | KIF18B | Hs.135094 | AA292789 |
| 64 | 202069_s_at | IDH3A | Hs.591110 | AI826060 |
| 65 | 203362_s_at | MAD2L1 | Hs.591697 | NM_002358 |
| 66 | 202666_s_at | ACTL6A | Hs.435326 | NM_004301 |
| 67 | 204892_x_at | EEF1A1 | Hs.520703 | NM_001402 |
| 68 | 205682_x_at | APOM | Hs.534468 | NM_019101 |
| 69 | 209714_s_at | CDKN3 | Hs.84113 | AF213033 |
| 70 | 218381_s_at | U2AF2 | Hs.528007 | NM_007279 |
| 71 | 201947_s_at | CCT2 | Hs.189772 | NM_006431 |
| 72 | 212722_s_at | JMJD6 | Hs.514505 | AK021780 |
| 73 | 204825_at | MELK | Hs.184339 | NM_014791 |
| 74 | 203184_at | FBN2 | Hs.519294 | NM_001999 |
| 75 | 201266_at | TXNRD1 | Hs.708065 | NM_003330 |
| 76 | 202969_at | DYRK2 | Hs.173135 | AI216690 |
| 77 | 204817_at | ESPL1 | Hs.153479 | NM_012291 |
| 78 | 209523_at | TAF2 | Hs.122752 | AK001618 |
| 79 | 218491_s_at | THYN1 | Hs.13645 | NM_014174 |
| 80 | 217363_x_at | — | — | AL031313 |
| 81 | 218009_s_at | PRC1 | Hs.567385 | NM_003981 |
| 82 | 204026_s_at | ZWINT | Hs.591363 | NM_007057 |
| 83 | 218355_at | KIF4A | Hs.648326 | NM_012310 |
| 84 | 202153_s_at | NUP62 | Hs.574492 | NM_016553 |
| 85 | 213011_s_at | TPI1 | Hs.524219 | BF116254 |
| 86 | 217966_s_at | FAM129A | Hs.518662 | NM_022083 |
| 87 | 214782_at | CTTN | Hs.596164 | AU155105 |
| 88 | 217967_s_at | FAM129A | Hs.518662 | AF288391 |
| 89 | 204649_at | TROAP | Hs.524399 | NM_005480 |
| 90 | 35671_at | GTF3C1 | Hs.371718 | U02619 |
| 91 | 213502_x_at | LOC91316 | Hs.148656 | AA398569 |
| 92 | 221285_at | ST8SIA2 | Hs.302341 | NM_006011 |
| 93 | 221519_at | FBXW4 | Hs.500822 | AF281859 |
| 94 | 202551_s_at | CRIM1 | Hs.699247 | BG546884 |
| 95 | 217138_x_at | IGL@ | Hs.449585 | AJ249377, | and wherein Table 1-1 and Table 1-2 are:

TABLE 1-1

| Gene Number | Probe Set. ID | Gene Symbol | UniGene.ID |
|---|---|---|---|
| 1 | 219306_at | KIF15 | Hs.646856 |
| 2 | 218585_s_at | DTL | Hs.656473 |
| 3 | 221677_s_at | DONSON | Hs.436341 |
| 4 | 201088_at | KPNA2 | Hs.594238 |
| 5 | 209034_at | PNRC1 | Hs.75969 |
| 6 | 202610_s_at | MED14 | Hs.407604 |
| 7 | 218906_x_at | KLC2 | Hs.280792 |

TABLE 1-1-continued

| Gene Number | Probe Set. ID | Gene Symbol | UniGene.ID |
|---|---|---|---|
| 8 | 212723_at | JMJD6 | Hs.514505 |
| 9 | 222231_s_at | LRRC59 | Hs.370927 |
| 10 | 208838_at | CAND1 | Hs.546407 |
| 11 | 218039_at | NUSAP1 | Hs.615092 |
| 12 | 209472_at | CCBL2 | Hs.481898 |
| 13 | 212898_at | KIAA0406 | Hs.655481 |
| 14 | 202620_s_at | PLOD2 | Hs.477866 |
| 15 | 201059_at | CTTN | Hs.596164 |
| 16 | 201841_s_at | HSPB1 | Hs.520973 |
| 17 | 203755_at | BUB1B | Hs.631699 |
| 18 | 211750_x_at | TUBA1C | Hs.719091 |
| 19 | 38158_at | ESPL1 | Hs.153479 |
| 20 | 204709_s_at | KIF23 | Hs.270845 |
| 21 | 201589_at | SMC1A | Hs.211602 |
| 22 | 218460_at | HEATR2 | Hs.535896 |
| 23 | 207430_s_at | MSMB | Hs.255462 |
| 24 | 212139_at | GCN1L1 | Hs.298716 |
| 25 | 211596_s_at | LRIG1 | Hs.518055 |
| 26 | 212160_at | XPOT | Hs.85951 |
| 27 | 219238_at | PIGV | Hs.259605 |
| 28 | 203432_at | TMPO | Hs.11355 |
| 29 | 201377_at | UBAP2L | Hs.490551 |
| 30 | 218875_s_at | FBXO5 | Hs.520506 |
| 31 | 221922_at | GPSM2 | Hs.584901 |
| 32 | 218727_at | SLC38A7 | Hs.10499 |
| 33 | 207469_s_at | PIR | Hs.495728 |
| 34 | 218483_s_at | C11orf60 | Hs.533738 |
| 35 | 204641_at | NEK2 | Hs.153704 |
| 36 | 219502_at | NEIL3 | Hs.405467 |
| 37 | 209054_s_at | WHSC1 | Hs.113876 |
| 38 | 220318_at | EPN3 | Hs.670090 |
| 39 | 210297_s_at | MSMB | Hs.255462 |
| 40 | 209186_at | ATP2A2 | Hs.506759 |
| 41 | 219787_s_at | ECT2 | Hs.518299 |
| 42 | 45633_at | GINS3 | Hs.47125 |
| 43 | 200848_at | AHCYL1 | Hs.705418 |
| 44 | 200822_x_at | TPI1 | Hs.524219 |
| 45 | 211072_x_at | TUBA1B | Hs.719075 |
| 46 | 200811_at | CIRBP | Hs.634522 |
| 47 | 202864_s_at | SP100 | Hs.369056 |
| 48 | 202154_x_at | TUBB3 | Hs.511743 |
| 49 | 213152_s_at | SFRS2B | Hs.476680 |
| 50 | 209368_at | EPHX2 | Hs.212088 |

| Gene Number | GenBank Accession Number | Weight Coefficient |
|---|---|---|
| 1 | NM_020242 | 0.5960 |
| 2 | NM_016448 | 1.4097 |
| 3 | AF232674 | 0.4683 |
| 4 | NM_002266 | 1.0480 |
| 5 | AF279899 | −1.4059 |
| 6 | AF135802 | −0.0393 |
| 7 | NM_022822 | 0.0880 |
| 8 | AK021780 | 0.3141 |
| 9 | AK025328 | 0.6264 |
| 10 | AB020636 | 0.2207 |
| 11 | NM_016359 | 1.5846 |
| 12 | BC000819 | −1.7235 |
| 13 | AB007866 | 0.1172 |
| 14 | NM_000935 | 1.3605 |
| 15 | NM_005231 | 0.3591 |
| 16 | NM_001540 | 1.2420 |
| 17 | NM_001211 | 0.9909 |
| 18 | BC005946 | 0.0145 |
| 19 | D79987 | 0.5325 |
| 20 | NM_004856 | 0.0798 |
| 21 | D80000 | 0.3106 |
| 22 | NM_017802 | 0.0198 |
| 23 | NM_002443 | 1.9177 |
| 24 | D86973 | −0.0501 |
| 25 | AB050468 | −2.0999 |
| 26 | AI984005 | 0.3461 |
| 27 | NM_017837 | −1.2689 |
| 28 | AW272611 | 0.4665 |
| 29 | NM_014847 | 0.1269 |
| 30 | NM_012177 | 0.1012 |
| 31 | AW195581 | 0.4423 |
| 32 | NM_018231 | −0.0411 |
| 33 | NM_003662 | 0.8827 |

TABLE 1-1-continued

| | | |
|---|---|---|
| 34 | NM_020153 | −1.3198 |
| 35 | NM_002497 | 1.5825 |
| 36 | NM_018248 | −0.1883 |
| 37 | AF083389 | 0.0465 |
| 38 | NM_017957 | 0.3073 |
| 39 | U22178 | 1.6681 |
| 40 | M23114 | 0.2014 |
| 41 | NM_018098 | 0.8181 |
| 42 | AI421812 | −0.2363 |
| 43 | AA479488 | −1.5895 |
| 44 | NM_000365 | 0.0814 |
| 45 | BC006481 | 0.0380 |
| 46 | NM_001280 | −1.4620 |
| 47 | NM_003113 | −1.3947 |
| 48 | NM_006086 | 0.1241 |
| 49 | AI343248 | −1.2495 |
| 50 | AF233336 | −1.8835 |

TABLE 1-2

| Gene Number | Probe Set. ID | Gene Symbol | UniGene.ID |
|---|---|---|---|
| 51 | 211058_x_at | TUBA1B | Hs.719075 |
| 52 | 209251_x_at | TUBA1C | Hs.719091 |
| 53 | 213646_x_at | TUBA1B | Hs.719075 |
| 54 | 204540_at | EEF1A2 | Hs.433839 |
| 55 | 202026_at | SDHD | Hs.719164 |
| 56 | 201090_x_at | TUBA1B | Hs.719075 |
| 57 | 213119_at | SLC36A1 | Hs.269004 |
| 58 | 217840_at | DDX41 | Hs.484288 |
| 59 | 206559_x_at | EEF1A1 | — |
| 60 | 202066_at | PPF1A1 | Hs.530749 |
| 61 | 203108_at | GPRC5A | Hs.631733 |
| 62 | 218697_at | NCKIPSD | Hs.655006 |
| 63 | 222039_at | KIF18B | Hs.135094 |
| 64 | 202069_s_at | IDH3A | Hs.591110 |
| 65 | 203362_s_at | MAD2L1 | Hs.591697 |
| 66 | 202666_s_at | ACTL6A | Hs.435326 |
| 67 | 204892_x_at | EEF1A1 | Hs.520703 |
| 68 | 205682_x_at | APOM | Hs.534468 |
| 69 | 209714_s_at | CDKN3 | Hs.84113 |
| 70 | 218381_s_at | U2AF2 | Hs.528007 |
| 71 | 201947_s_at | CCT2 | Hs.189772 |
| 72 | 212722_s_at | JMJD6 | Hs.514505 |
| 73 | 204825_at | MELK | Hs.184339 |
| 74 | 203184_at | FBN2 | Hs.519294 |
| 75 | 201266_at | TXNRD1 | Hs.708065 |
| 76 | 202969_at | DYRK2 | Hs.173135 |
| 77 | 204817_at | ESPL1 | Hs.153479 |
| 78 | 209523_at | TAF2 | Hs.122752 |
| 79 | 218491_s_at | THYN1 | Hs.13645 |
| 80 | 217363_x_at | — | — |
| 81 | 218009_s_at | PRC1 | Hs.567385 |
| 82 | 204026_s_at | ZWINT | Hs.591363 |
| 83 | 218355_at | KIF4A | Hs.648326 |
| 84 | 202153_s_at | NUP62 | Hs.574492 |
| 85 | 213011_s_at | TPI1 | Hs.524219 |
| 86 | 217966_s_at | FAM129A | Hs.518662 |
| 87 | 214782_at | CTTN | Hs.596164 |
| 88 | 217967_s_at | FAM129A | Hs.518662 |
| 89 | 204649_at | TROAP | Hs.524399 |

TABLE 1-2-continued

| | | | |
|---|---|---|---|
| 90 | 35671_at | GTF3C1 | Hs.371718 |
| 91 | 213502_x_at | LOC91316 | Hs.148656 |
| 92 | 221285_at | ST8SIA2 | Hs.302341 |
| 93 | 221519_at | FBXW4 | Hs.500822 |
| 94 | 202551_s_at | CRIM1 | Hs.699247 |
| 95 | 217138_x_at | IGL@ | Hs.449585 |

| Gene Number | GenBank Accession Number | Weight Coefficient |
|---|---|---|
| 51 | BC006379 | 0.0646 |
| 52 | BC004949 | 0.0453 |
| 53 | BE300252 | 0.0396 |
| 54 | NM_001958 | 1.8487 |
| 55 | NM_003002 | −1.3587 |
| 56 | NM_006082 | 0.0733 |
| 57 | AW058600 | 0.0680 |
| 58 | NM_016222 | 0.0313 |
| 59 | NM_001403 | −0.9727 |
| 60 | AA195259 | 0.7385 |
| 61 | NM_003979 | 1.0799 |
| 62 | NM_016453 | −0.0693 |
| 63 | AA292789 | 0.6820 |
| 64 | AI826060 | 0.2302 |
| 65 | NM_002358 | 0.8095 |
| 66 | NM_004301 | 0.2162 |
| 67 | NM_001402 | −0.9566 |
| 68 | NM_019101 | −1.0558 |
| 69 | AF213033 | 0.9594 |
| 70 | NM_007279 | −0.0076 |
| 71 | NM_006431 | 0.2632 |
| 72 | AK021780 | 0.0968 |
| 73 | NM_014791 | 1.1379 |
| 74 | NM_001999 | 0.7174 |
| 75 | NM_003330 | 0.2610 |
| 76 | AI216690 | 0.2560 |
| 77 | NM_012291 | 0.4866 |
| 78 | AK001618 | 0.3803 |
| 79 | NM_014174 | −1.3652 |
| 80 | AL031313 | −0.9838 |
| 81 | NM_003981 | 1.6691 |
| 82 | NM_007057 | 0.9942 |
| 83 | NM_012310 | 1.1017 |
| 84 | NM_016553 | −0.0983 |
| 85 | BF116254 | 0.1005 |
| 86 | NM_022083 | −2.4459 |
| 87 | AU155105 | 0.2306 |
| 88 | AF288391 | −2.7067 |
| 89 | NM_005480 | 0.1495 |
| 90 | U02619 | 0.0169 |
| 91 | AA398569 | −2.1336 |
| 92 | NM_006011 | −0.9209 |
| 93 | AF281859 | −1.1897 |
| 94 | BG546884 | −2.0141 |
| 95 | AJ249377 | −1.0505. |

2. The method for examining prognosis of breast cancer according to claim 1, wherein the expression level is determined by using a microarray having at least the nucleic acid described in Table 1-1-1 and Table 1-2-1.

* * * * *